(12) United States Patent
Powers et al.

(10) Patent No.: US 10,029,108 B2
(45) Date of Patent: Jul. 24, 2018

(54) ADAPTIVE SELF-TESTING AND STRESS ANALYSIS OF MEDICAL DEVICES

(71) Applicant: KONINKLIJKE PHILIPS N.V., Eindhoven (NL)

(72) Inventors: Daniel J. Powers, Issaquah, WA (US); Carlton B. Morgan, Bainbridge Island, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/442,012

(22) PCT Filed: Dec. 3, 2013

(86) PCT No.: PCT/IB2013/060585
§ 371 (c)(1),
(2) Date: May 11, 2015

(87) PCT Pub. No.: WO2014/097035
PCT Pub. Date: Jun. 26, 2014

(65) Prior Publication Data
US 2015/0265844 A1    Sep. 24, 2015

Related U.S. Application Data

(60) Provisional application No. 61/738,099, filed on Dec. 17, 2012.

(51) Int. Cl.
*A61N 1/39*   (2006.01)

(52) U.S. Cl.
CPC ............. *A61N 1/3943* (2013.01); *A61N 1/39* (2013.01); *F04C 2270/041* (2013.01)

(58) Field of Classification Search
CPC .. A61N 1/3993; A61N 1/3925; A61N 1/3706; A61N 1/36142; A61N 1/39; A61N 1/37; A61N 2001/083; A61N 1/046; A61N 1/36125; A61N 1/025; A61N 1/08; A61N 1/362; A61N 1/00; A61N 1/0472; A61N 1/3943; G06F 19/3418; G06F 19/3406; G06F 19/3412; A61B 5/4836; A61B 5/02; A61B 5/02438; A61B 2560/0276; G06Q 50/22
See application file for complete search history.

(56) References Cited

U.S. PATENT DOCUMENTS 5,579,234 A * 11/1996 Wiley ..................... A61N 1/39
702/118
5,591,213 A    1/1997 Morgan
(Continued)

FOREIGN PATENT DOCUMENTS

| CN | 101119766 A | 2/2008 |
| CN | 101204605 A | 6/2008 |
| WO | 2006055936 A2 | 5/2006 |

*Primary Examiner* — Deborah Malamud

(57) ABSTRACT

An improved self-testing method is described which is incorporated into a defibrillator (20). The method performs a self-testing protocol which operates on a first frequency until a threshold condition is reached. When the threshold condition is reached, the self-testing protocol switches to a second frequency. Such a method enables quicker identification of a failure mode in a population of defibrillators, while maintaining acceptable battery life in the device.

9 Claims, 5 Drawing Sheets

(56) References Cited

U.S. PATENT DOCUMENTS

| | | |
|---|---|---|
| 5,782,878 A | 7/1998 | Morgan et al. |
| 5,800,460 A | 9/1998 | Powers et al. |
| 5,868,792 A | 2/1999 | Ochs et al. |
| 5,899,925 A | 5/1999 | Ochs et al. |
| 5,955,956 A | 9/1999 | Stendahl et al. |
| 5,964,786 A | 10/1999 | Ochs et al. |
| 6,185,458 B1 | 2/2001 | Ochs et al. |
| 6,329,822 B1 | 12/2001 | Powers et al. |
| 6,381,492 B1 | 4/2002 | Rockwell et al. |
| 2008/0147136 A1 | 6/2008 | Zhou et al. |
| 2010/0023074 A1 | 1/2010 | Powers et al. |
| 2010/0150246 A1 | 6/2010 | Naclerio |
| 2012/0123241 A1 | 3/2012 | Stilley et al. |

* cited by examiner

ADAPTIVE SELF-TESTING AND STRESS ANALYSIS OF MEDICAL DEVICES

CROSS-REFERENCE TO PRIOR APPLICATIONS

This application is the U.S. National Phase application under 35 U.S.C. § 371 of International Application No. PCT/IB2013/060585, filed on Dec. 3, 2013, which claims the benefit of U.S. Provisional Patent Application No. 61/738,099, filed on Dec. 17, 2012. These applications are hereby incorporated by reference herein.

This invention relates to an improvements in automatic self-testing of medical devices. The present invention is particularly useful for a device such as an automatic external defibrillator (AED) that normally operates in a standby mode for long periods of time between uses.

Electro-chemical activity within a human heart normally causes the heart muscle fibers to contract and relax in a synchronized manner that results in the effective pumping of blood from the ventricles to the body's vital organs. Sudden cardiac death is often caused by ventricular fibrillation (VF) in which abnormal electrical activity within the heart causes the individual muscle fibers to contract in an unsynchronized and chaotic way. The only effective treatment for VF is electrical defibrillation in which an electrical shock is applied to the heart to allow the heart's electro-chemical system to re-synchronize itself. Once organized electrical activity is restored, synchronized muscle contractions usually follow, leading to the restoration of cardiac rhythm. But it is critical to defibrillate VF within just a few minutes after its onset for the treatment to be effective.

The necessity to apply defibrillation quickly after the onset of VF has given rise to automatic external defibrillators (AEDs) which may be used by first responders and lay people. AEDs may remain unused for long periods of time and yet must be ready to operate reliably in an emergency situation. To ensure operational readiness, most AEDs employ a self-test operation that is conducted at regular intervals. The Heartstream Forerunner AED manufactured by Philips Medical Systems of Andover Mass., for example, employs a self-test system that generates self-test operations automatically in response to a predetermined schedule. The self-test operation typically includes a number of different system checks including functional, calibration, and safety tests to verify that the defibrillator's components and operation are within predetermined specifications. The high voltage (HV) circuit is a critical component of the defibrillator that provides the defibrillation pulse. Verification of the proper functioning of the high voltage circuit of a defibrillator is a typical part of any self-test operation.

U.S. Pat. No. 5,591,213, "Defibrillator System Condition Indicator" (Morgan et al.), describes a defibrillator system which includes means for periodically operating a high voltage circuit to discharge a test pulse to a test load. Such self-tests may be done periodically or in response to changes in the defibrillator environment such as the ambient temperature as described in U.S. Pat. No. 5,868,792, "Environment-Response Method for Maintaining Electronic Devices Such As An External Defibrillator" (Ochs et al.) which is incorporated herein by reference. A similar invention described in U.S. Pat. No. 5,964,786, entitled "Environment-Responsive Method for Maintaining an Electronic Device," incorporated herein by reference, utilizes an internal self-testing protocol which defers the self-test schedule for a time based on changes in the device temperature.

U.S. Pat. No. 5,800,460, "Method for Performing Self-Test in a Defibrillator" (Powers et al.) describes in detail the operation of a defibrillator self-test system. An energy storage capacitor is twice charged to full voltage and discharged, first to functionally verify operation of the HV circuit under combined maximum voltage and current conditions and second to calibrate the HV circuit to ensure that the amount of energy delivered in the defibrillation pulse is within specification limits. The test load is resistance typically in the range of 10 ohms.

Providing a test pulse to the test load at a combined maximum voltage and maximum current stress as taught by Powers et al. results in a substantial amount of energy dissipated in the test load for each self-test operation. The self-test of the HV circuit forms only a portion of the overall defibrillator self-test but consumes the majority of total energy that is required over the four-or-five year design life of a battery. The AED must therefore be designed with a larger battery than if self-testing was not performed.

One prior art invention which incorporates a method for reducing the energy required to perform a self-test of the HV circuit is described in U.S. Pat. No. 6,185,458, entitled "Reduced Energy Self-Test Operation in a Defibrillator." The method described in this patent applies voltage and current stresses to the HV components equivalent to operating conditions, but only partially charges the HV energy source to conserve battery life.

Another prior art invention automatically adjusts the protocol or periodicity of a self-test depending on the type of power source that is connected to the defibrillator. U.S. Pat. No. 6,185,458, entitled "Periodic automatic self-test system and methodology", is herein incorporated by reference.

Each of the aforedescribed patents is directed to identifying failures in AEDs before they are used in a cardiac arrest rescue, but without unduly shortening the AED battery life. All incorporate a self-testing protocol which does not vary in frequency or periodicity after the protocol is established.

Three basic failure modes in a population of AEDs have been identified, each of which prevails during a particular phase of the AED life. FIG. 1 illustrates these theoretical failure modes on a curve known as the Weibull curve of theoretical observed failure rate 17. Observed failure rate 17 is the combination of the infant mortality failure rate 14, the random failure rate 15, and the wear-out failure rate 16.

Infant mortality is expected to be the prevalent mode of AED failure during the first phase 11 of the product life. Infant mortality failures are associated with defects such as material defects, design errors, or errors in assembly. Such defects may be undiscoverable by in-factory testing. The failure may also be lot-related. As devices with such defects fail and are removed from service, the infant mortality failure rate falls to a negligible level.

Random failures are normally considered to be random cases of "stress exceeding strength." Random failures may occur at a relatively constant rate over the life of an AED population due to mishaps, exposure to extreme environmental conditions, and the like. Random failures are assumed to be the primary mode of failure during the middle of the AED life, as shown in region 12.

The third mode of failure, wear-out 16, is generally due to fatigue or depletion of materials. In an AED, some components such as batteries and electrodes are expected to become depleted with time and may be routinely replaced as wear-out failures are detected or according to their expiration dates. Overall, however, a typical AED useful service life is limited by its shortest-lived component. As each AED nears the end of its useful life at region 13, the observed failure rate 17 will increase again as various components fail with age.

The observed failure rate 17 for AEDs is typically very low and thus requires long periods of time before a statistically significant failure population is established. Years of data may be necessary to identify a cause of failure which indicates the appropriate corrective action. By that time, a very large population of AEDs may be affected. If the corrective action requires a recall, only a few of the recalled AEDs may actually have the defect that requires the corrective action. Thus, the manufacturer experiences unnecessary expense and wasted time, and public safety is compromised due to devices being needlessly been removed from service. What is needed is a faster and more effective way of identifying device failures in order to minimize the number of devices which require corrective action.

The observed failure rate data for several models of AEDs has been closely analyzed by the inventors. The data suggests that latent defects in components or defects introduced from manufacturing processes may persist for extended periods before precipitating a failure. That is, the infant mortality curve 14 of FIG. 1 may add a considerable contribution to the overall failure rate for an extended period of time. Latent defects in components may therefore cause the device to fail prematurely in the field, but may not arise during product testing in the factory. The data also suggests that the AED self-test itself applies sufficient cyclic stress to the device to eventually force the latent defect to manifest itself as a device failure. Much like fatigue failure, the HV self-test in particular applies sufficient voltage, current and heat to stress the AED components into a self-test failure. The HV self-test may be even more effective at doing so at the device design margins of environmental conditions such as temperature, humidity, condensation, shock, and vibration.

Prior art HV self-tests are applied at most on a weekly basis throughout the AED lifetime. This protocol may result in a latent defect failure that occurs much later in AED life than if the HV self-test were run more often. But HV self-tests consume substantial power, so that all present art AEDs run them infrequently in order to conserve battery life.

On the other hand, low voltage (LV) self-tests have been observed not to have much effect on latent defect detection. Because LV self-tests consume little power, they are usually run on a daily basis.

In accordance with the principles of the present invention, an improved medical device and method for automatically self-testing the medical device are described. The method for self-testing comprises periodically performing a self-test protocol at a first frequency, detecting a condition which exceeds a threshold condition, automatically switching the self-test protocol to a second frequency responsive to the detecting step, and periodically performing the self-test protocol at the second frequency. The threshold condition may be a predetermined elapsed time, an environmental condition, or a sensed rate at which the AED is actually used. If the self-test protocol is an HV self-test, the first frequency should be higher than the second frequency. If the self-test protocol is an LV self-test, the second frequency may be as low as zero. By appropriately selecting the two frequencies of self-test for each protocol, battery life of the medical device may be maximized. The device incorporating the method may be an AED.

In accordance with a further aspect of the principles of the present invention, another embodiment of an improved medical device and method for automatically self-testing the medical device is described. This embodiment includes the self-test protocol steps having two different testing frequencies, but further includes a receiving step which controls the switch from the first to the second frequency of testing. The receiving step receives information that a second medical device having a temporally similar manufacturing date is defective. The device incorporating the method may be an AED with a wireless receiver.

In accordance with a further aspect of the present invention an improved visual indicator for displaying the operational status of a defibrillator is described. The improved visual indicator comprises a light emitting diode (LED), a liquid crystal display (LCD), and a printed graphic icon which operate in concert to provide a clear indication of the device status.

Figure 1:
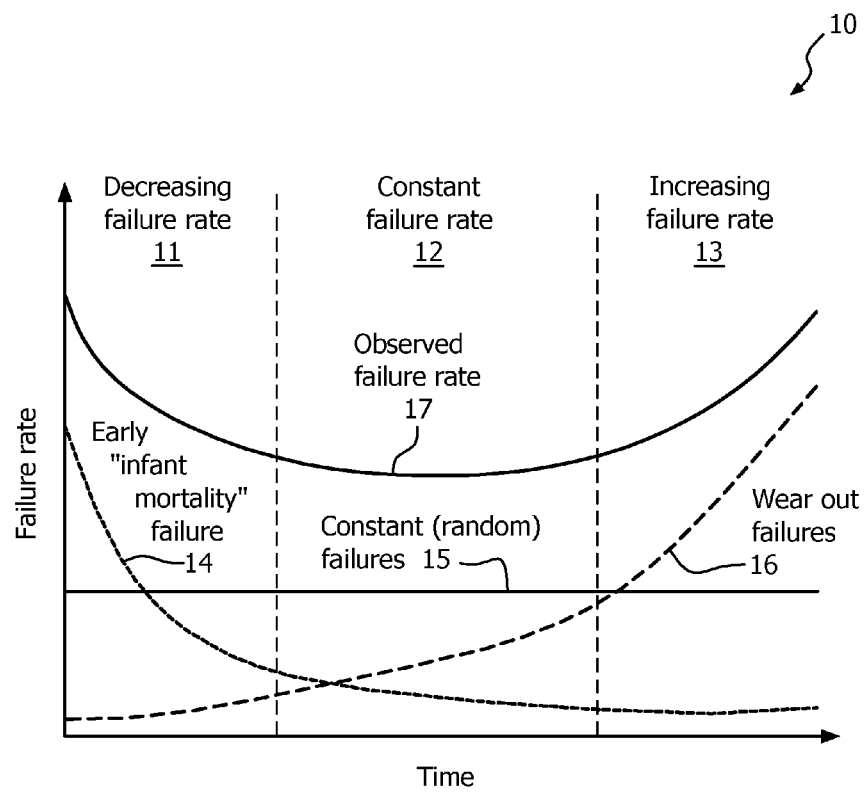
FIG. 1 illustrates a Weibull bathtub curve of theoretical observed failure rates.
Figure 2:
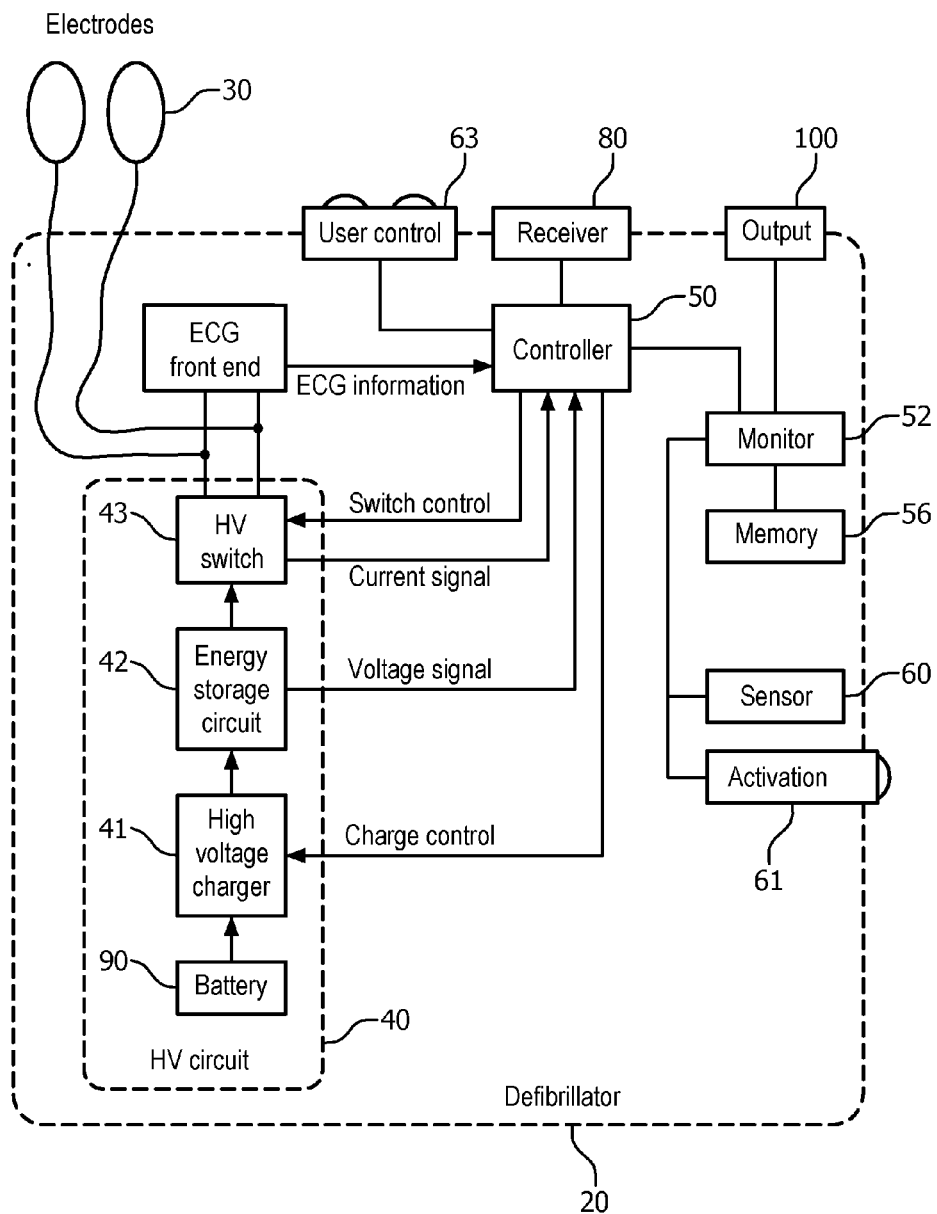
FIG. 2 is a block diagram showing the functional components of an external defibrillator according to one embodiment of the invention.

Turning to the illustrations, FIG. 2 is a functional block diagram of an exemplary medical device that incorporates the improved self-testing method according to one embodiment of the invention. In this embodiment, the medical device is an automatic external defibrillator (AED) 20 in which a pair of electrodes 30 are coupled across the chest of a patient (not shown) to apply high voltage defibrillation therapy during a cardiac rescue. The electrodes 30 are coupled to an ECG front end which filters, amplifies, and digitizes the ECG signals from the patient to obtain ECG information which is provided to a controller 50. A shock advisory algorithm executed by controller 50 analyzes the ECG signals to detect a shockable rhythm such as ventricular fibrillation (VF). If a shockable rhythm is detected, controller 50 causes a defibrillation pulse to be delivered to the patient via a high voltage (HV) circuit 40. Controller 50 may receive user input from a user control input 63 in order to control the delivery of the shock, and/or to control other aspects of the AED during the cardiac rescue. User control input 63 may be implemented as one or more push buttons or the equivalent.

The HV circuit 40 contains an HV switch 43 that is coupled to the pair of electrodes 30, an energy storage circuit 42 coupled to the HV switch 43, and a high voltage charger 41 for charging the energy storage circuit 42 to the desired charge level. In the preferred embodiment, the HV switch 43 is constructed as an H bridge as is known in the art.

Energy storage circuit 42 is coupled to the HV switch 43 to provide the high voltage, high current waveform necessary to develop the defibrillation pulse. The energy storage circuit 42 typically consists of at least one capacitor with a capacitance value in the range of 100 to 200 microfarads (uF) and which is charged to approximately 2000 volts. The high voltage charger 41 converts the relatively low battery voltage, typically approximately 12 volts, from a battery 90 to the relatively high voltage levels required to charge the energy storage circuit 42.

Controller 50, implemented for example with a general purpose microprocessor, an embedded controller, or a state machine, operates to control the functions of the defibrillator 20 including the self-test operation according to the present invention. The HV switch 43 develops the defibrillation pulse responsive to a switch control signal from the controller 50 in the desired polarity and pulse duration. The voltage of the energy storage circuit 42 is controlled through via the charge control signal to the high voltage charger 41 from the controller 50. The parameters for the HV components during self-test and actual use are similar. Discharge of the energy during self-test occurs through a simulated patient load that may be incorporated within HV switch 43 instead of through the patient electrodes.

During the self-test operation, a current signal from the HV switch 43 and a voltage signal from the energy storage circuit 42 may be fed back to the controller 50 which evaluates the results of the self-test operation. If the self-test operation is not within predetermined parameters, the defibrillator 20 issues an alert through its output 100. Otherwise, output 100 indicates that the defibrillator 20 is ready to use. Output 100 may be an aural indicator, a visual indicator, or preferably a combination of the two. In addition, output 100 may be in communication with a remote location. By this means, output 100 indicates the result of the most recent self-testing operation.

If an undetected latent defect exists in one of the components in HV circuit 40, the voltage and current stresses imposed by repeated applications of the self-test operation may eventually cause the component to fail. The failure is normally discovered during the self-test (or the subsequent self-test) and is communicated to the user via the output 100.

FIG. 2 also shows a system monitor 52 which controls the scheduling of the self-tests. During standby, circuitry except for monitor 52 remains de-energized in order to conserve battery power. Monitor 52, which is a processor preferably operating at low power, operates in a low-power mode during standby to operate a clock, to drive a readiness indicator at output 100, and to sense an environmental or other condition at sensor 60. Preferably, system monitor 52 controls the initiation of self-tests at controller 50 by "waking up" the controller 50 on a periodic schedule or in response to some sensed environmental condition from sensor 60 that calls for a self-test. Monitor 52 may also sense a user activation of the AED from user activation input 61. User activation of the device may in turn initiate a startup-self-test at the beginning of a cardiac rescue. User activation input 61 may be disposed as a push button, a lever, or some other suitable on/off element.

A memory 56 contains instructions and parameters for the self-testing schedule, the self-testing protocol, and threshold conditions that control a modification of the self-testing schedule. Memory 56 may also store the results of self-tests, and historical environmental data such as temperature, mechanical shocks, and humidity. Memory 56 may additionally retain device use information, such as the number or rate of device activations at activation input 61 as sensed by controller 50 and/or monitor, the sensed number or rate of user button presses at user control 63 or the number of defibrillator shocks that have been delivered.

The threshold conditions necessary to modify the self-testing schedule will be described in more detail with regards to the discussion of the methods. Threshold conditions are those that indicate that a different frequency of self-testing would be more beneficial for identifying defects and for conserving battery power. For example, a threshold condition may be an elapsed time from the first AED activation, a predetermined rate of device activations by a user, a predetermined number of user button presses, a temperature above or below the normal design operating temperature range, a predetermined number of mechanical shocks to the device, or a humidity threshold. The threshold conditions are compared against a corresponding sensed condition to reduce HV self-testing frequency after a threshold elapsed time, to increase HV self-testing frequency after a predetermined number of mechanical shocks or in the presence of high humidity, and so on.

Sensor 60 detects a condition which can be compared to a threshold condition. Sensor 60 thus may be disposed to detect environmental conditions such as temperature, mechanical shock, or humidity/internal moisture. Thus, sensor 60 may be a temperature sensor, an accelerometer, a force sensor, or a moisture sensor. Sensor 60 could also be disposed as an elapsed timer or a counter which estimates elapsed time since the device was placed into service. Sensor 60 could also be disposed as a counter of user button presses or as a sensor of the rate at which the device is activated by a user.

After the initial activation of the defibrillator outside of the factory, controller 50 operates in concert with the "wake up" system monitor 52 to periodically operate the defibrillator circuitry in a self-testing protocol at a first frequency. After each self-test, the result is indicated at output 100. The controller 50 compares a sensed condition against a predetermined threshold condition. If the sensed condition exceeds the threshold condition, controller 50 causes a switch to be set in memory 56 which shifts the self-testing protocol to a second frequency by means of the system monitor 52.

Preferably, the nature of the self-testing protocol itself remains the same regardless of the frequency that it is conducted. For example, controller 50 and monitor 52 could conduct a HV self-test protocol on a daily basis upon initial activation of the AED by the customer. After a certain number of daily HV self-tests, controller 50 and monitor 52 could switch the HV self-test protocol to a weekly or monthly frequency in order to conserve battery power. Under this arrangement, it is expected that latent defects which can be uncovered by the stress of HV self-testing will manifest themselves sooner than in the prior art devices.

Alternatively, the second frequency could be set higher than the first frequency if a condition exceeding a threshold condition indicates that the defibrillator 20 exists in a relatively harsh operating environment. Presumably, such an environment would arise with higher-use defibrillators, such as with first responder owners, e.g., emergency medical services. For these owners, the reduced battery life resulting from a more frequent self-testing schedule would be acceptable in light of the reliability assurance of a more rigorous self-testing schedule.

Another embodiment of the defibrillator 20 includes a receiver 80 which is in communication with controller 50. Receiver 80 is preferably operable to wirelessly receive information from a remote location that collects and analyzes data from the entire population of defibrillators. Receiver 80 can be of wireless Internet, cellular telephony, Bluetooth™ radio, infrared, optical, or the like. Receiver 80 can additionally or alternately be wire-connected to a network for the receipt of this information, such as a data network in the facility where the defibrillator is stored in readiness for use.

Preferably, the information includes data regarding self-test failures or other identified defects in like defibrillators. The sibling defibrillators may have a temporally similar manufacturing date, or otherwise may have been constructed from similar lots of components or processes which have been identified as being potentially defective. Receiver 80 communicates the information to controller 50, which in response switches the self-testing protocol to a second, preferably higher, frequency. The higher frequency self-testing will then presumably enjoy a higher likelihood of identifying a latent defect during self-testing.

Figure 3:
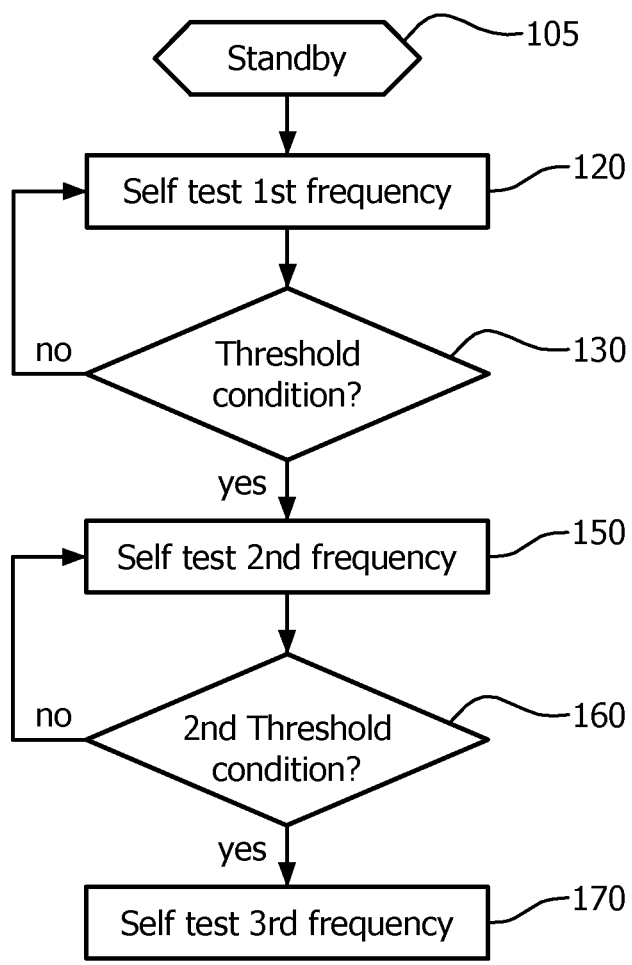
FIG. 3 illustrates a flow chart showing one embodiment of the inventive method.

FIG. 3 describes a method according to one implementation of the present invention. After the end user receives the defibrillator 20 from the manufacturer, the end user prepares the defibrillator 20 for use and places the device into a standby state at step 105. Step 105 is typically accomplished by unpacking the defibrillator, applying battery power to the device, running a battery insertion self-test, and then placing the device in an accessible storage location. Thereafter, at step 120, the defibrillator 20 periodically activates itself to conduct a self-testing protocol at a first frequency according to instructions residing in the device memory 56. One example of a self-testing protocol is a HV self-test which exercises the high voltage circuitry in the defibrillator. A preferred first frequency of the HV self-test according to one embodiment of the present invention is on a daily basis. As previously discussed, the heightened frequency of stress-testing the HV components by this method step may cause a device to fail due to a latent defect earlier in the product life. Earlier detection results in earlier diagnosis and reduced costs of corrective action. If the device fails a self-test, it provides an output 100 alert which brings the failure to the user's attention. Otherwise, the device provides an output of "ready-to-use" and proceeds to the next step 130.

Defibrillator 20 automatically checks a condition against a threshold level at step 130 each time that defibrillator 20 activates for self-testing. As previously discussed, the condition could be an elapsed time and the corresponding threshold level a predetermined time period such as an infant mortality period. Alternatively, an environmental condition and environmental threshold could correspond to a temperature, a level of mechanical shock, or a humidity level. Another alternative threshold is a use condition such as the number of times a control button at input 63 has been pressed by the user or the number of times a user has activated the AED at activation input 61.

If the condition does not exceed the threshold level at step 130, defibrillator 20 returns to standby after the self-test and thereafter repeats the self-testing protocol at the first frequency step 120.

A detected condition which exceeds the threshold level at step 130 may indicate that the self-testing protocol can be further optimized if it is conducted at a second frequency. In response to such a detected condition, defibrillator 20 automatically switches the self-testing protocol to the second frequency of self-testing at step 150. Defibrillator 20 then returns to standby. Thereafter, defibrillator 20 periodically activates to conduct the self-testing protocol at the second frequency. The previous example of the HV self-test could have a second frequency of monthly or less frequently in order to conserve battery life. Thus, the first HV self-test frequency is higher than the second frequency.

The above method of performing a self-testing protocol at two different frequencies depending on a detected condition may also be applied to low voltage (LV) self-testing. In prior art devices, the LV self-test is performed on a daily basis throughout the defibrillator operating lifetime. Analysis of failure rate data for several models of defibrillators suggests that a daily LV self-test may be unnecessary after the infant mortality phase 11 but prior to the wear-out phase 13. Consequently, the first frequency of LV self-testing may be higher than the second frequency. Whereas a preferred first frequency is daily, a second frequency for an LV self-test may be zero.

The method illustrated in FIG. 3 optionally comprises a step 160 of checking a condition against a second threshold level. Step 160 is conducted during or immediately after the self-test step 150 at the second frequency. The second threshold may be the same or may be different in nature than the threshold condition at step 130. If the second threshold level is not exceeded at step 160, the self-test continues at the 2nd frequency at step 150. However, if the second threshold level is exceeded at step 160, the self-test is changed to a third frequency.

The condition and second threshold level at step 160 may in one embodiment relate to a battery replacement in the defibrillator. A threshold number of detected battery replacements may indicate that the defibrillator is nearing the end of its design life where a device failure becomes more likely and where an increase in self-test frequency may be desired. Thus, step 160 may compare a count of battery replacements to a threshold level of a predetermined number of battery replacements. Upon detection of a particular battery replacement, the defibrillator automatically switches the performance of the self-test protocol to the third frequency, and performs the self-test at step 170 thereafter. The third frequency may be between the first and second frequencies.

Alternatively, the condition and the second threshold level may relate to an elapsed time and a second predetermined period of time following the start of the second-frequency self-test protocol of step 150. Such an elapsed time may also indicate that the defibrillator is nearing the end of its design life where a device failure becomes more likely and where an increase in self-test frequency may be desired. When the elapsed time exceeds the second threshold at step 160, the defibrillator automatically switches the self-test protocol to the third frequency and thereafter periodically performs the self-test protocol at the third frequency in step 170. The third frequency in this case is higher than the second frequency.

Figure 4:
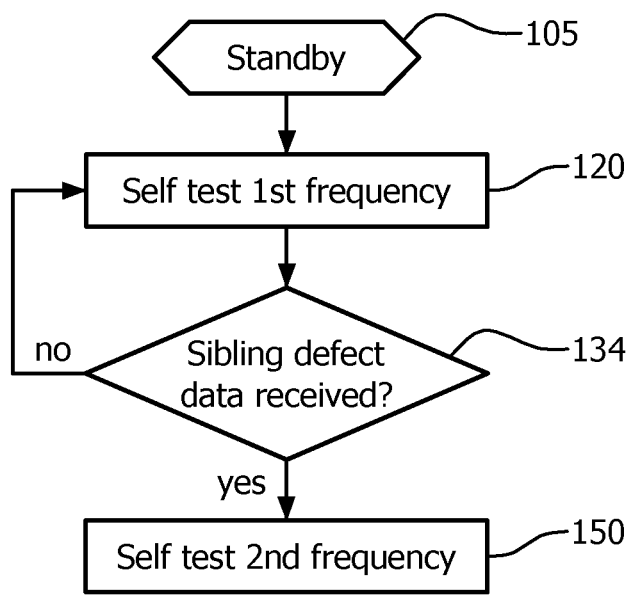
FIG. 4 illustrates a flow chart showing another embodiment of the inventive method.

In FIG. 4, another embodiment of the invention is described. Similar to the FIG. 3 method, a step 105 of placing the defibrillator in standby is followed by the initiation of periodic performance of a self-test protocol at a first frequency at step 120. The FIG. 4 method, however, contemplates the use of a defibrillator which comprises a receiver for receiving information from a remote location. The information preferably relates to failures or defects in defibrillators of the same model, and more preferably relates to failures or defects in defibrillators having a temporally similar manufacturing date or with components of the same lot as the defibrillator. The received information is stored in the defibrillator memory 56 for later retrieval.

The receiver preferably receives information via a wireless communication path. The reception of information may occur during appropriate times and according to known receiving methods. For example, if the defibrillator wireless receiver is configured to receive only during the self-test period, a method of synchronizing transmissions from the remote location to the defibrillator may be desirable in order to conserve battery power. Other receiving methods may allow the defibrillator to receive at any time during standby, when activated for use, or during self-testing periods.

After each performance of the self-test protocol at the first frequency at step 120, the defibrillator automatically checks its memory for received information at step 134. If the received information pertains to a second defibrillator, e.g. a sibling defibrillator, which has a temporally similar manufacturing date, the defibrillator automatically switches its self-test protocol to a second frequency at step 150. Alternatively, the received information may pertain to a shared lot for a defibrillator component which has or potentially has a latent defect.

The self-test protocol is thereafter conducted at the second frequency. Typically the second frequency at step 150 is higher than the first frequency at step 120. The FIG. 4 method thus increases the level of self-testing on defibrillators which may potentially have a greater probability for failure due to an experienced failure of sibling defibrillators or shared component lots.

Figure 5A:
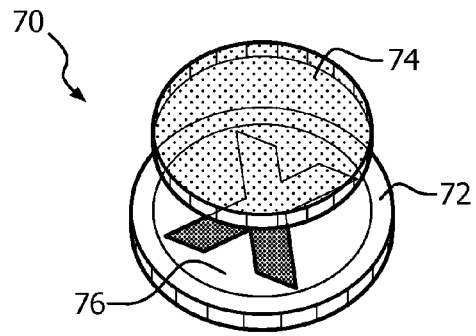
FIGS. 5a through 5d illustrate an improved visual indicator for indicating the readiness status of a medical device such as an AED.

FIG. 5a illustrates an output 100 disposed on an exterior surface of defibrillator 20. Here, output 100 comprises a visual indicator 70 that operates to indicate the result of a self-testing protocol. Visual indicator 70 thus provides a readiness state output to the user. In a preferred embodiment, system monitor 52 powers the visual indicator 70.

As shown in FIG. 5a, visual indicator 70 comprises three main elements. A base layer contains a graphic icon 76 that symbolizes a "Not Okay" state, such as a red "X" symbol. Surrounding the graphic icon 76 is/are one or more colored LEDs 72. LEDs 72 are arranged around the periphery of graphic icon 76, and are preferably driven by monitor 52 in a flashing mode to conserve battery power. In one embodiment, red LEDs, signifying "Not Okay", and green LEDs, signifying "Ready for Use", are collectively arranged around the periphery of graphic icon 76. An LCD shutter 74 is arranged to overlie graphic icon 76 but not LEDs 72. LCD shutter 74 is biased so as to be opaque when driven by the system monitor 52. When not driven, LCD 74 is transparent such that graphic icon 76 is visible.

Figure 5B:
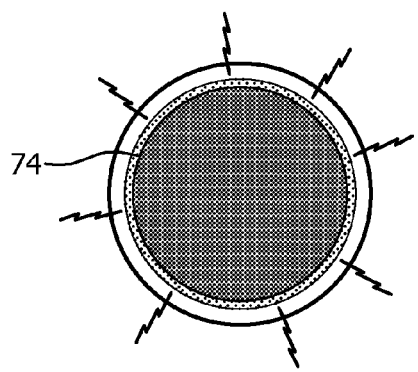
Figure 5C:
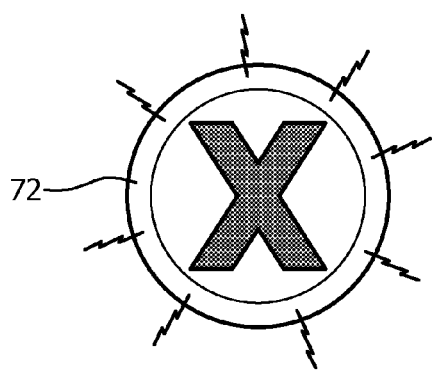
Figure 5D:
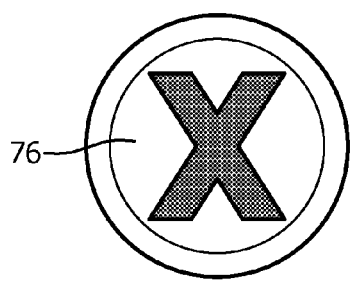

FIGS. 5b through 5d illustrate the operation of visual indicator 70. In FIG. 5b, defibrillator 20 has successfully passed the most recent self-testing protocol. System monitor 52 thus drives LCD shutter 74 to opaque in order to obscure the graphic icon 76. Preferably, system monitor 52 also drives the peripheral green LEDs 72 to illuminate. The FIG. 5b green state of the indicator shows that the defibrillator 20 is ready for use. The FIG. 5b state may also be used to signify that the self-testing protocol has been modified according to the previously described method. For example, if self-testing has been automatically switched to a second frequency, system monitor 52 may drive a non-green or non-red LED 72, such as yellow, to illuminate. Thus, the user would be alerted that, although the defibrillator 20 is ready for use, some potential condition has driven the defibrillator 20 into a different self-testing frequency. This would allow the user to investigate further if necessary or desired.

In FIG. 5c, the defibrillator 20 self-testing protocol has identified a failure or potential failure. In this state, system monitor 52 causes LCD shutter 74 to become transparent and thus expose the "Not Okay" graphic icon 76. In addition, system monitor 52 may drive red LEDs 72 to illuminate steadily or periodically to attract further attention to the device. Thus, the user is alerted to begin corrective action. Alternatively, in the case of identification of a potential failure, the "Not Okay" graphic icon 76 could be exposed while illuminating a non-red LED 72 to indicate that the defibrillator is operational, but a potential problem has been identified which may cause an impending failure. Such a problem might be identified by received information or by the switch to a different self-testing frequency.

FIG. 5d illustrates the indication when defibrillator 20 has completely failed. In this case, no power is needed for the visual indicator 70 at all. When there is no power available to illuminate LED 72, there is also no power to cause LCD 74 to obscure the "Not Okay" graphic icon 72. Thus, visual indicator 70 is a fail-safe indicator for a non-functional defibrillator 20.

The primary advantages of the visual display 70 of the preferred embodiment are its low power requirements and its fail-safe nature. Display 70 improves upon the prior art indicators by providing the user with both an illuminated LED alert as well as a graphic indication of device status that provides a functional indication even if no power is available for LED illumination.

Modifications to the device, method, and displays as described above are encompassed within the scope of the invention. For example, various configurations of the controller and monitor circuits which fulfill the objectives of the described invention fall within the scope of the claims. Also, the particular appearance and arrangement of the output alert at the defibrillator location may differ. Different self-testing protocols which perform essentially the same predictive functions as described also fall within the scope of the invention.

What is claimed is:

1. A method for self-testing a defibrillator, comprising the steps of:
   periodically performing a self-test protocol at a first frequency;
   detecting a condition which exceeds a threshold condition;
   automatically switching the self-test protocol from the first frequency to a second frequency responsive to the detecting step; and
   periodically performing the self-test protocol at the second frequency,
   wherein the first frequency is higher than the second frequency,
   wherein the condition is an elapsed time and the threshold condition is a predetermined time period,
   wherein the second frequency is greater than zero.

2. The method of claim 1, further comprising the steps of:
   automatically switching the self-test protocol to a third frequency that is higher than the second frequency after a predetermined period of time following the start of the step of periodically performing the self-test protocol at the second frequency; and
   periodically performing the self-test protocol at the third frequency.

3. A method for self-testing a defibrillator, comprising the steps of:
   periodically performing a self-test protocol at a first frequency;
   detecting a condition which exceeds a threshold condition;
   automatically switching the self-test protocol from the first frequency to a second frequency responsive to the detecting step; and
   periodically performing the self-test protocol at the second frequency,
   wherein the first frequency is higher than the second frequency, wherein the condition is a number of completed self-tests and the threshold condition is a predetermined number of self-tests, wherein the second frequency is greater than zero.

4. A method for self-testing a defibrillator, comprising the steps of:
periodically performing a self-test protocol at a first frequency;
detecting a condition which exceeds a threshold condition;
automatically switching the self-test protocol from the first frequency to a second frequency responsive to the detecting step; and
periodically performing the self-test protocol at the second frequency,
wherein the first frequency is higher than the second frequency,
wherein the condition is an environmental condition and the threshold condition is an environmental threshold condition,
wherein the second frequency is greater than zero.

5. The method of claim 4, wherein the environmental condition is one selected from the set consisting of a temperature, a user activation, a mechanical shock, and a humidity.

6. A defibrillator having an automatic self-testing protocol, comprising:
a circuit for delivering high voltage electrotherapy to a pair of patient electrodes;
a memory storing instructions for a self-testing protocol and a threshold condition;
a sensor for detecting a condition corresponding to the threshold condition;
a controller coupled to the memory and sensor and operable to conduct a self-test of the defibrillator using the self-testing protocol at either a first frequency if the condition does not exceed the threshold condition or at a second frequency if the condition subsequently exceeds the threshold condition; and
an output that provides an indication of the result of the most recent self-test,
wherein the second frequency is lower than the first frequency, and further wherein the threshold condition is selected from one of the group consisting of an elapsed time, a predetermined number of user activations, a predetermined number of user control button presses, and a predetermined number of mechanical shocks,
wherein the second frequency is greater than zero.

7. The defibrillator of claim 6, wherein the output is a visual graphic which comprises a light emitting diode (LED), a liquid crystal display (LCD), and a graphic icon.

8. The defibrillator of claim 7, wherein the graphic icon indicates that the defibrillator is not ready for use,
wherein the LCD overlays the printed graphic icon and is operable to obscure the graphic icon when the defibrillator is ready for use, and
wherein the LED is operable to illuminate when the defibrillator is ready for use.

9. A defibrillator having an automatic self-testing protocol, comprising:
a circuit for delivering high voltage electrotherapy to a pair of patient electrodes;
a memory storing instructions for a self-testing protocol and a threshold condition;
a sensor for detecting a condition corresponding to the threshold condition;
a controller coupled to the memory and sensor and operable to conduct a self-test of the defibrillator using the self-testing protocol at either a first frequency if the condition does not exceed the threshold condition or at a second frequency if the condition exceeds the threshold condition; and
an output that provides an indication of the result of the most recent self-test, wherein the second frequency is lower than the first frequency,
further comprising a receiver operable to wirelessly receive information that a second defibrillator having a temporally similar manufacturing date is defective,
wherein the controller is further operable to operate the circuit in the self-testing protocol at a third frequency that is higher than the first frequency in response to the received information.

* * * * *